(12) United States Patent
Wang et al.

(10) Patent No.: US 9,856,482 B2
(45) Date of Patent: Jan. 2, 2018

(54) SPECIFIC OLIGONUCLEOTIDE APTAMER FOR THE IDENTIFICATION OF T-2 TOXIN

(71) Applicant: Jiangnan University, Wuxi (CN)

(72) Inventors: Zhouping Wang, Wuxi (CN); Xiujuan Chen, Wuxi (CN); Huajie Gu, Wuxi (JP); Yu Xia, Wuxi (CN); Shijia Wu, Wuxi (CN); Nuo Duan, Wuxi (CN); Xiaoyuan Ma, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 14/909,743

(22) PCT Filed: May 26, 2015

(86) PCT No.: PCT/CN2015/079797
§ 371 (c)(1),
(2) Date: Feb. 3, 2016

(87) PCT Pub. No.: WO2016/011845
PCT Pub. Date: Jan. 28, 2016

(65) Prior Publication Data
US 2017/0121715 A1    May 4, 2017

(30) Foreign Application Priority Data

Jul. 24, 2014    (CN) .......................... 2014 1 0357649

(51) Int. Cl.
*C12N 15/11* (2006.01)
*C12N 15/115* (2010.01)
*G01N 33/53* (2006.01)

(52) U.S. Cl.
CPC ....... *C12N 15/115* (2013.01); *G01N 33/5308* (2013.01); *C12N 2310/16* (2013.01); *C12N 2320/13* (2013.01)

(58) Field of Classification Search
None
See application file for complete search history.

*Primary Examiner* — Ekaterina Poliakova-Georgantas
(74) *Attorney, Agent, or Firm* — Gokalp Bayramoglu

(57) ABSTRACT

This invention provides a small molecule oligonucleotide aptamer binding to T-2 toxin specifically, and the sequence of the ssDNA aptamer is SEQ ID NO: 1. Through the graphene oxide separation-based Systematic Evolution of Ligands by Exponential Enrichment, single-stranded oligonucleotide aptamer with high affinity and specific identification of T-2 toxin was obtained in vitro selection. The aptamer has a broad application prospect, which can be used for separation and enrichment of trace T-2 toxin in the sample. It can also be used as a reporter aptamer for the detection of T-2 toxin in food by means of functional groups labeling and other means.

2 Claims, 2 Drawing Sheets

SEQUENCE LISTING

```
<160> NUMBER OF SEQ ID NOS: 7

<210> SEQ ID NO 1
<211> LENGTH: 80
<212> TYPE: DNA
<213> ORGANISM: artificial sequence
<220> FEATURE:
<223> OTHER INFORMATION: synthesized

<400> SEQUENCE: 1
cagctcagaa gcttgatcct gtatatcaag catcgcgtgt ttacacatgc gagaggtgaa      60
cagatgcacg acttcgagtc                                                   80

<210> SEQ ID NO 2
<211> LENGTH: 78
<212> TYPE: DNA
<213> ORGANISM: artificial sequence
```

```
<220> FEATURE:
<223> OTHER INFORMATION: synthesized

<400> SEQUENCE: 2
cagctcagaa gcttgatcct tagcacacaa ccctttgatt gggatatctc atccctcgga      60
ctcgaagtcg tgcatctg                                                    78

<210> SEQ ID NO 3
<211> LENGTH: 80
<212> TYPE: DNA
<213> ORGANISM: artificial sequence
<220> FEATURE:
<223> OTHER INFORMATION: synthesized

<400> SEQUENCE: 3
cagctcagaa gcttgatcct accacagcca gtaagtcccg taggccctgg ttgggctgtt      60
gactcgaagt cgtgcatctg                                                  80

<210> SEQ ID NO 4
<211> LENGTH: 80
<212> TYPE: DNA
<213> ORGANISM: artificial sequence
<220> FEATURE:
<223> OTHER INFORMATION: synthesized

<400> SEQUENCE: 4
cagctcagaa gcttgatcct gtatatcaag catcgcgtgt ttacacatgc gagaggtgaa      60
gactcgaagt cgtgcatctg                                                  80

<210> SEQ ID NO 5
<211> LENGTH: 38
<212> TYPE: DNA
<213> ORGANISM: artificial sequence
<220> FEATURE:
<223> OTHER INFORMATION: synthesized

<400> SEQUENCE: 5
tagcacacaa ccctttgatt gggatatctc atccctcg                              38

<210> SEQ ID NO 6
<211> LENGTH: 40
<212> TYPE: DNA
<213> ORGANISM: artificial sequence
<220> FEATURE:
<223> OTHER INFORMATION: synthesized

<400> SEQUENCE: 6
accacagcca gtaagtcccg taggccctgg ttgggctgtt                            40

<210> SEQ ID NO 7
<211> LENGTH: 40
<212> TYPE: DNA
<213> ORGANISM: artificial sequence
<220> FEATURE:
<223> OTHER INFORMATION: synthesized

<400> SEQUENCE: 7
gtatatcaag catcgcgtgt ttacacatgc gagaggtgaa                            40
```

SPECIFIC OLIGONUCLEOTIDE APTAMER FOR THE IDENTIFICATION OF T-2 TOXIN

CROSS-REFERENCE TO RELATED APPLICATIONS

This application claims priority from CN Application No. 201410357649.9, filed Jul. 24, 2014 and PCT Application No. PCT/CN2015/079797, filed May 26, 2015, the contents of which are incorporated herein in the entirety by reference.

FIELD OF THE INVENTION

The invention relates to biological technology field, specifically involves oligonucleotide aptamers against T-2 toxin with high affinity and specificity through a SELEX technology (Systematic Evolution of Ligands by Exponential Enrichment, SELEX). It lay a solid foundation for the rapid separation, enrichment and analysis of T-2 toxin.

BACKGROUND OF THE INVENTION

T-2 toxin (T-2), a sesquiterpene compound, is one of the most toxic in trichothecene mycotoxins. It produced by various species of *Fusarium*, mainly from *F. acuinatum, F. poae, F. langsethiae,* and *F. sporotrichioide* with an extensive distribution and be seriously harmful to the health of human and livestock. Toxic effects of T-2 include acute toxicity, subacute toxicity, chronic toxicity, three induced effects, immune toxicity and damage to blood system and soft tissue. The toxicity of T-2 toxin is quite stable. Its toxicity is still not reduced when it is placed for 6 to 7 years under room temperature or heated for 1 hour by 100-120° C. Due to its severe toxicity, international attaches great importance to the harm of T-2 toxin to human and livestock. Early in 1973, T-2 toxin was ranked as one of the most dangerous source of food pollution in nature by FAO/WHO. More extensive and in-depth researches on T-2 toxin have been carried out after the "Yellow rain poisoning" incident.

Recently, measurement methods available for T-2 toxin mainly include thin layer chromatography (TLC), gas chromatography (GC), liquid chromatography (LC), liquid chromatography/mass spectrometry (LC-MS), enzyme linked immunosorbent assay (ELISA) and so on. TLC is cheap in analytical cost, but suffer the problems of tedious operations and weak reducibility. GC and LC methods cannot directly determine T-2 toxin in samples and need a derivatization process. The derivatization of T-2 toxin for GC method mainly based on trimethyl silylation and fluorine acetoxylation. The derivatization reagent for LC method is Isocyanate. And the toxic chemical reagent was used in the process of measurement. LC-MS method offers the merits of sensitivity, simplicity in sample preparation, and no need for derivatization processing, but is expensive in cost. Antibody-based immunoassay often possesses the advantages of simple operation, high sensitivity, availability for a large number of samples, and no need for large and expensive equipment. However, it also suffer from the problems including the false positive rate is relatively high, and the quantity is not accurate enough. Moreover, as a small molecule semi antigen with a molecular weight of 466 g/mol, T-2 toxin does not have immunogenicity so that it is necessary to combine with the large molecule carrier protein to prepare the complete antigen to stimulate the secretion of antibodies. The process is not only cumbersome, time-consuming and costly, but the stability of the antibody batches produced is not as high as the oligonucleotide. And the antibody storage conditions are also more stringent than the oligonucleotide.

Recent years, as a potential substitute for antibody, the study on oligonucleotides aptamer is more eye-catching. Aptamers are a cluster of small molecules DNA or RNA fragments generated by systemic evolution of ligands by exponential enrichment (SELEX) technology and can selectively bind to their target molecules. SELEX technology is a new combined chemical technology developed in 1990s, which has the characteristics of economy, simple, rapid, wide application range and so on. SELEX technology using molecular biological technology to construct the synthetic random oligonucleotide library in which the middle random sequence length generally is about 20-40 nt and the primer sequences at both ends generally is about 20 nt. The library capacity is about $10^{13}$-$10^{15}$ range. Because the single stranded oligonucleotide random sequence is easy to form convex ring, hair clips, holidays, G tetramer as secondary structure, it can combine with protein, peptides, drugs, amino acids, organic compounds, and even metal ions to form the complex with a very strong bonding force.

SUMMARY OF THE INVENTION

Technical Problems

Until now, the reported aptamers against fungaltoxin are mainly prepared by SELEX selection process through immobilizing the targets onto the surface of affinity chromatography or magnetic beads. The former is used for ochratoxin A, the latter is used forfumonisin B1. Some other labs also reported the aptamers selection against zearalenone based on affinity chromatography or magnetic beads method. But there is no report dealt with aptamer of T-2 toxin and the preparation of it.

Technology Solutions

The purpose of the present invention is to provide oligonucleotide aptamers specially binding to T-2 toxin with high affinity, laying foundation for the development of new separation and/or analysis tools for T-2 toxin.

Another purpose of the present invention is to provide a preparation method of T-2 toxin oligonucleotide aptamers, which is accurate and convenient to obtain high affinity of single-strand DNA aptamers against T-2 toxin.

The invention utilizes the SELEX technology based on graphene oxide separation, taking T-2 toxin as target and no need to immobilize the target onto the carrier. The enriched library sequences after 10 rounds of repeated screening were cloned and sequenced. The affinity and specificity of candidate sequences were analyzed, and oligonucleotide aptamers with high affinity and specificity for T-2 toxin were obtained ultimately.

Beneficial Effect

In this invention, T-2 toxin, often be found in food or feed, used as the target to utilize graphene oxide (GO) separation-based SELEX technology to select aptamer with high affinity and specificity. The aptamer can be used for the separation and concentration of trace T-2 toxin in samples, and also can be used for testing T-2 toxin after modified by special groups to enrich the detection method in laboratory. It can also be used to develop test strips or portable small instruments to achieve rapid detection in families, farms and factories. Therefore, the invention can be widely applied in the field of mycotoxin detection.

DETAILED DESCRIPTION OF PARTICULAR EMBODIMENTS OF THE INVENTION

Figure 1:
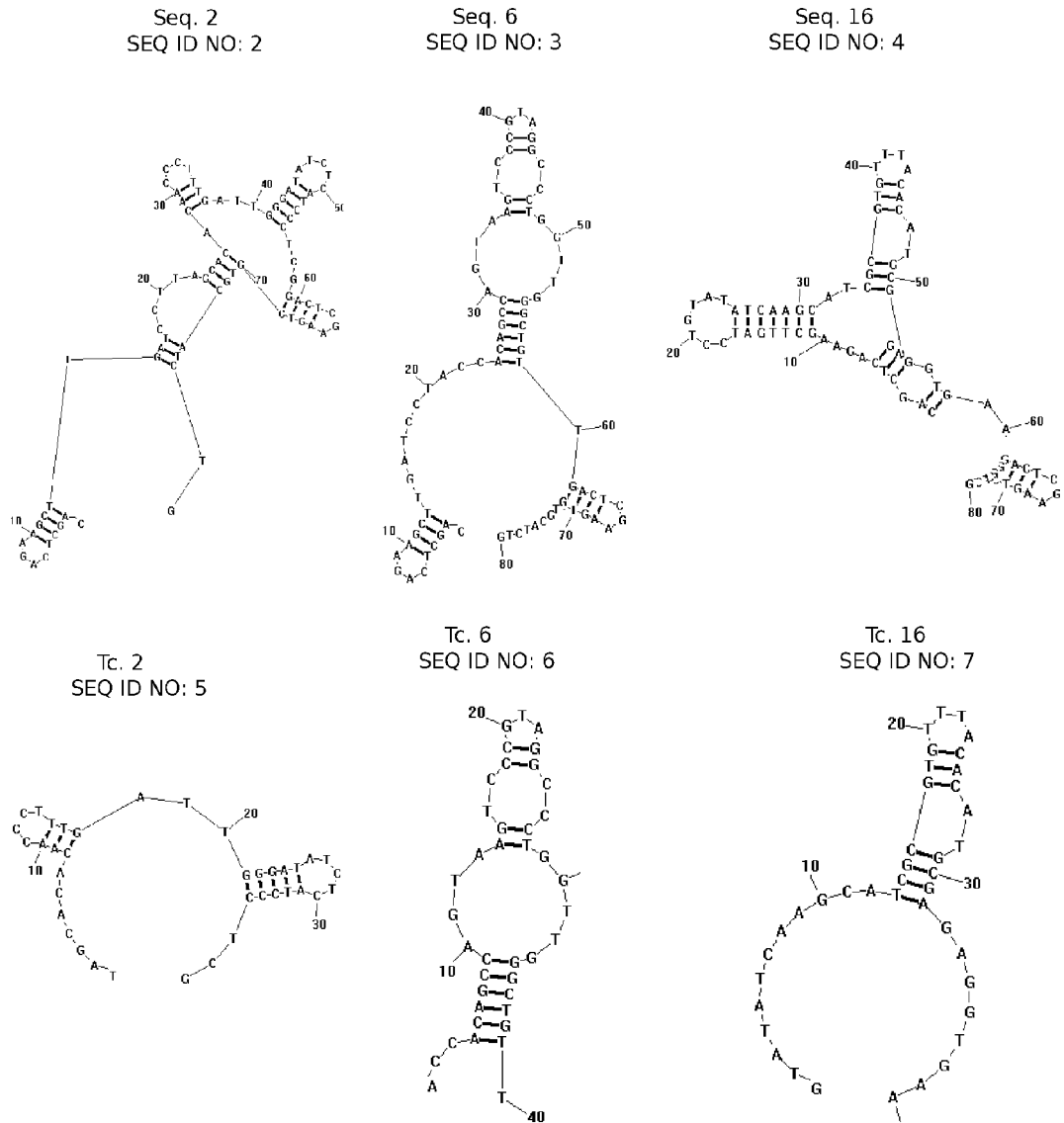
FIG. 1 is the simulated secondary structure models of full-length aptamers and their truncated sequences.
Figure 2:
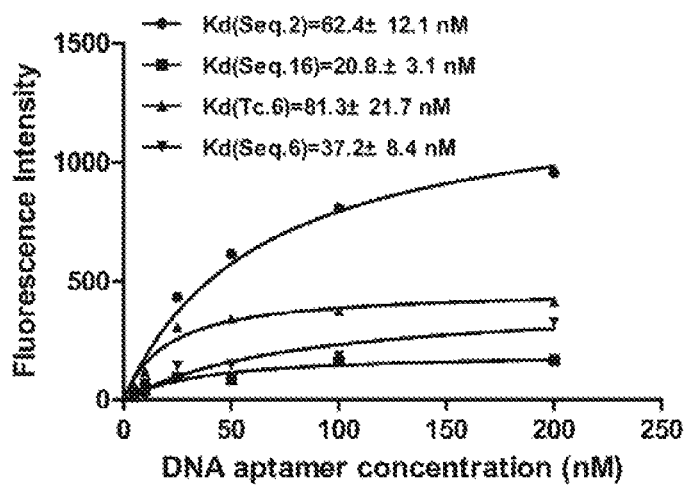
FIG. 2 is the saturation binding curve of Seq. 2, Seq. 6, Seq. 16 and Tc. 6 oligonucleotide aptamers.
Figure 3:
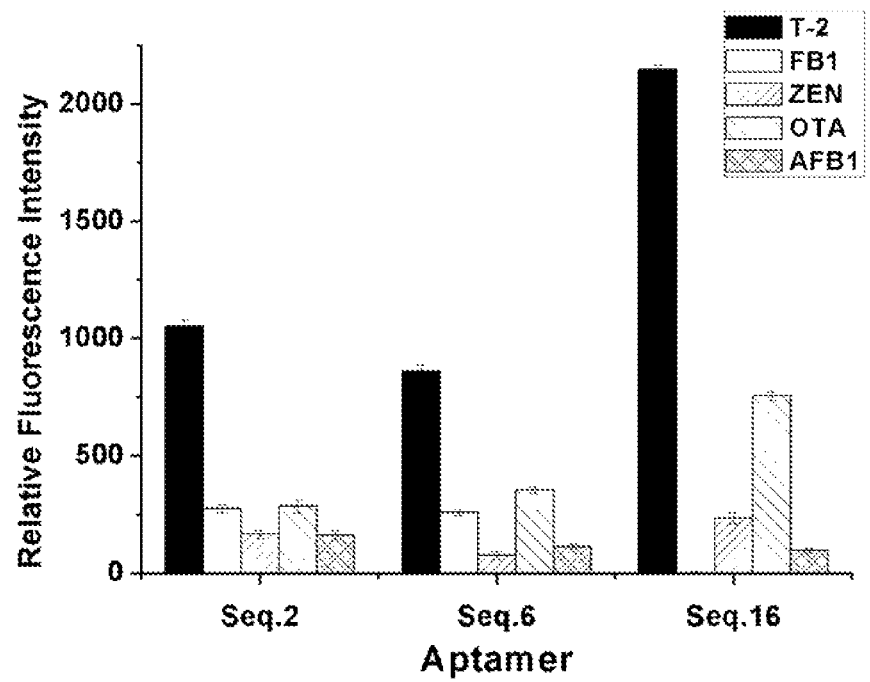
FIG. 3 is the specific test results of Seq. 2, Seq. 6 and Seq. 16 oligonucleotide aptamers.

According to the figures and instructions for further explanation of the embodiment of the invention, but not limited for the invention.

Example 1

GO-SELEX Selection of Oligonucleotides Aptamer Specific Binding to T-2 Toxin 1. In vitro chemical synthesis of initial random single strand DNA (ssDNA) library and primers (completed by the United States Integrated Technologies DNA company), the sequence as follows:

```
5'-CAGCTCAGAAGCTTGATCCT-N40-
GACTCGAAGTCGTGCATCTG-3',
N40 represents 40 random nucleotides.

Forward primer:
5'-CAGCTCAGAAGCTTGATCCT-3';

Reverse primer:
5'-P-CAGATGCACGACTTCGAGTC-3';

Phosphorylated reverse primer:
5'-P-CAGATGCACGACTTCGAGTC-3'.
```

The random ssDNA library and primers were prepared into 100 μM storage solution with TE buffer with stored in −20° C. backup.

2. Conditions of PCR amplification and preparation of single stranded sub library by Lambda exonuclease digestion The synthesized random single stranded library (ssDNA) was diluted and used as template to produce phosphorylated double stranded DNA (dsDNA) product amplified by PCR. The influence factors of the preparation of single stranded sub library by digesting phosphorylated antisense strand with Lambda exonuclease were also studied. Ultimately the optimum conditions for the preparation of the single stranded sub library was determined.

The PCR reaction system: Diluted random library as DNA template 1 μL (100 ng), the forward primer and Phosphorylated reverse primer (20 μM) 1 μL, dNTPmix (each 25 mm) 1 μL, 10×PCR amplification buffer 5 μL, sterile ultra pure water 40 μL, Taq enzyme 1 μL, the total volume is 50 μL. PCR amplification procedures: 94° C. predenaturation 5 min; 94° C. denaturation 30 s; 53° C. annealing 30 s; 72° C. extension 20 s; loop 20 times; the last 72° C. extension for 5 min. The results were verified by 8% non denaturing polyacrylamide gel electrophoresis.

The PCR amplification products with correct electrophoresis position and being single were purified by PCR product purification kit (Generay Biotech. Co., Ltd), resoluted in appropriate volume sterilizing ultrapure water, measured by thermo NanoDrop 2000 ultra-trace spectrophotometer to determine the concentration of dsDNA. Took the purified PCR product solution with determined concentration, added definited exonuclease (5 U/μL) and ⅒ volume of 10× reaction solution, uniformly mixed, 37° C. reacted for 30 min~60 min and 75° C. in water bath for 10 min to stop the reaction by deactivating the enzyme. Through the 8% 7 M urea denaturated polyacrylamide gel electrophoresis, the best conditions for the enzyme digestion was determined and then conducted the amplified enzyme digestion. The digestion products were collected together in a 1.5 ml centrifuge tube, added same volume of phenol:chloroform: isoamyl alcohol (V:V:V=25:24:1), vortex mixed tube contents to make it in the emulsion, 12000 rpm centrifugated for 15 s at 4° C. The upper liquid then was carefully moved into another centrifuge tube, abandoned the two-phase interface and the organic phase. Repeated operation once, until the two phase interface cannot see the protein so far. The ⅒ volume of 3 M sodium acetate (pH 5.2) solution and 2 times volume of anhydrous alcohol was added to the centrifuge tube containing the sample, fully mixed and then put into the −20° C. freezer over night. The tubes were balanced and centrifugated at 12000 rpm, 4° C. for 15 min. After discarding supernatant, 4° C. pre-cold 70% ethanol 0.5-1 mL was added to wash white solid precipitation upside down, and was centrifugated at 12000 rpm, 4° C. for 15 min. Discarded supernatant again, dry deposition, re-dissolved in the appropriate volume of buffer, determined the concentration of ssDNA with a Thermo NanoDrop 2000 ultra trace spectrophotometer.

3. In Vitro GO-SELEX Selection

In the first round selection, 1 nmol (the input amount of ssDNA library from second to the tenth round was reduced to 200 or 100 pmol) random ssDNA library dissolved in binding buffer (BB, 10 mM Tris-HCl, 150 mM NaCl, 10 mM KCl, and 2.5 mM $MgCl_2$, pH 7.4) was heated at 94° C. for 5 min, immediately cooled on ice for 15 min and placed at room temperature for 10 min. Next, the ssDNA library and the free target T-2 toxin were mixed evenly, and make it in special binding buffer containing 1% methanol (the total volume of 500 μL) incubated for 2 h with tilting and rotation. After the incubation, the mixture was transferred to the GO slice which was washed well by centrifugation, and was incubated at 25° C. for 40 min. The ssDNA sequences bound to T-2 target were retained in the supernatant, whereas the non-binding ssDNA sequences were absorbed by GO. The supernatant then was collected by 13000 rpm/min centrifugation for 10 min and the ssDNA aptamer library binding with T-2 toxin was obtained. The supernatant was used as amplification template to perform PCR amplification. And the ssDNA sub library were generated by lambda exonuclease digestion of the phosphorylated strands from purified dsDNA products. The concentration of purified ssDNA was determined by NanoDrop Thermo 2000 ultra-trace spectrophotometer, and the volume of the next round library was calculated according to it.

Counter GO-SELEX was performed from 6-10 round to improve the specificity of the aptamers against T-2. The ssDNA sub library (200 pmol) was firstly incubated with a mixture of FB1, ZEN, AFB1 and OTA for 60 min, and then GO slice was added evenly and incubated for 40 min. During this process, the oligonucleotides that did not bind to the counter-targets were adsorbed onto the GO surface by π-π stacking interactions, while those bound to the counter-targets remained suspended in the buffer. After separation by centrifugation, the GO on which oligonucleotides were adsorbed was resuspended and washed with BB for several time. Subsequently, target T-2 was mixed with the GO-ssDNAs and incubated further for 2 h at room temperature, to recover the aptamers from the GO surface. After the incubation, the mixture solution was centrifuged, and the supernatant was collected and amplified by PCR. The purified PCR products, the phosphorylated strands from dsDNA products, were digested again by lambda exonuclease to prepare the ssDNA sub library.

4. Cloning, Sequencing and Sequence Analysis

The $10^{th}$ round screened oligonucleotide aptamer enrichment library were amplified with unmodified primers. The purified PCR products were cloned with pMD-19T cloning vector (Takara Biotech. Co. Ltd) and transformed to calcium chloride competent cells of *E. coli* DH5α. After cultivated for 18 hours in solid culture medium containing 50 μg/mL ampicillin penicillin, through the "blue white screening" randomly selected 30 white positive clones were grown in LB liquid medium, and the plasmid was extracted with plasmid MiniPrep Kit (Generay Biotech. Co. Ltd.), then sent to Shanghai Biotechnology Company for sequencing. After sequencing, the successfully obtained 27 oligonucleotide aptamer sequences was analyzed using DNAMAN software for primary structure. Sequence homology information of multiple sequences was then obtained. And the secondary structure of each sequence was predicted using RNA structure 4.6 software. According to the characteristics of the primary and secondary structure of the T-2 toxin oligonucleotide aptamer, 27 sequences were divided into 3 families. From each of the families, one of sequences with lower level and stable structure was chose as representative. As shown in FIG. 1, the representative sequences Seq.2, Seq.6, Seq.16 and the truncated sequences Tc.2, Tc.6, Tc.16 were synthesized and labeled with 5'FAM group by Shanghai Sangon Biotech Company to make further affinity and specificity analysis.

5. Affinity and Specificity Analysis of T-2 Toxin 5.1 Affinity Analysis

In order to analyze the affinity of the three representative sequences and the truncated sequence, T-2 toxin with a fixed concentration (1 μM) was incubated with various concentrations (5, 10, 25, 50, 100, 200 nm) of the aptamer sequences, in 500 μL of volume, in the dark for 2 h. Then, GO proportional to the amount of aptamers present was added to each tube, and the mixture was incubated in the dark for 40 min. After centrifugation, the fluorescence intensity was measured using an F-7000 Fluorescence Spectrophotometer with excitation at 490 nm. Negative controls without T-2 added were used to determine nonspecific binding. The equilibrium dissociation constant (Kd) of oligonucleotide aptamer was determined using GraphPad Prism 5.0 software (as shown in Table 1).

TABLE 1

The dissociation constant Kd values of full-length and truncated sequences

| Aptamers No. | Kd (nM) |
|---|---|
| Seq. 2 | 62.4 ± 12.1 |
| Seq. 6 | 37.2 ± 8.4 |
| Seq. 16 | 20.8 ± 3.1 |
| Tc. 2 | n.d. |
| Tc. 6 | 81.3 ± 21.7 |
| Tc. 16 | n.d. |

FIG. 2 is the saturation binding curve of Seq. 2, Seq. 6, Seq. 16 and Tc. 6. The analysis showed that Seq. 2, Seq. 6 and Seq. 16 are the sequences with the strongest affinity and the smallest Kd values to T-2 toxin.

5.2 Specificity Analysis

Three sequences (Seq. 2, Seq. 6 and Seq. 16) were selected to evaluate the specificity of the aptamers against T-2 toxin based on the assay results of Section 5.1. The 5'FAM-labeled oligonucleotides aptamers were mixed with target T-2 or FB1, ZEN, AFB1, and OTA, respectively, then incubated with GO solution (final concentration 0.3 mg/mL) for 2 h at room temperature in the dark. The negative control for each sequence was mixed with BB instead of any mycotoxin targets. Subsequently, each of the mixtures was centrifuged at 13000 rpm/min for 10 min, and the supernatant was collected and measured using an F-7000 Fluorescence Spectrophotometer with excitation at 490 nm. The results showed that the binding ability of T-2 toxin aptamers to target T-2 toxin were stronger than those of the other four kinds of mycotoxins. The specificity test results as shown in FIG. 3.

The invention includes but is not limited to the embodiment of the invention, any equivalent replacement or partial in the spirit and principle of the present invention shall be deemed to be within the scope of the protection of the present invention.

What is claimed is:

1. A specific oligonucleotide aptamer for the identification of T-2 toxin comprising SEQ ID NO: 1.

2. The oligonucleotide aptamer as in claim 1, which is chemically modified in the 5' or 3' end with FITC, amino group, biotin or digoxin.

* * * * *